United States Patent [19]

Brennan et al.

[11] 4,049,657

[45] Sept. 20, 1977

[54] PREPARATION OF N-(AMINOALKYL)PIPERAZINE

[75] Inventors: Michael E. Brennan; Philip H. Moss; Ernest L. Yeakey, all of Austin, Tex.

[73] Assignee: Texaco Development Corporation, New York, N.Y.

[21] Appl. No.: 583,019

[22] Filed: June 2, 1975

[51] Int. Cl.$^2$ .................. C07D 295/12; C07D 241/00
[52] U.S. Cl. ............................................. 260/268 SY
[58] Field of Search .................................. 260/268 SY

[56] References Cited

U.S. PATENT DOCUMENTS 3,121,115  2/1964  Meuly ............................. 260/583 P Primary Examiner—Donald G. Daus
Assistant Examiner—Jose Tovar
Attorney, Agent, or Firm—Carl G. Ries; Thomas H. Whaley

[57] ABSTRACT

An improved process for selectively preparing an N-(aminoalkyl)piperazine compound is disclosed wherein piperazine is contacted with a primary or secondary amino alkanol compound in the presence of a catalytically effective amount of a phosphorus-containing substance at a temperature of from about 250° to about 350° C under a pressure sufficient to maintain the mixture essentially in liquid phase and the N-(aminoalkyl)piperazine is then recovered from the resultant reaction mixture. In a preferred embodiment piperazine is contacted with monoethanolamine to produce N-(2-aminoethyl)-piperazine.

8 Claims, No Drawings

PREPARATION OF N-(AMINOALKYL)PIPERAZINE

BACKGROUND OF THE INVENTION

1. Field of the Invention

This invention relates to the selective preparation of N-(aminoalkyl)piperazine and more particularly pertains to a direct liquid phase catalytic process for synthesizing predominantly non-polymer N-(aminoalkyl)piperazines.

2. Prior Art

There are several procedures described in the literature for directly preparing predominantly noncyclic alkyleneamines by the condensation reaction of an amino-alkanol compound and an alkylatable amine compound which do not require neutralization of the reaction product to obtain the desired salt-free polyamines.

For example, U.S. Pat. No. 3,714,259 to Lichtenwalter et al. describes a catalytic process for the preparation of polyethylene polyamines whereby an ethyleneamine compound and an ethanolamine compound are contacted in the presence of hydrogen and a hydrogenation catalyst comprised of oxides of nickel, copper, chromium, and like metals, in liquid phase at a temperature of 140° C to 170° C. This procedure has been shown to require extended reaction times to provide acceptable conversions and yields of the polymeric polyethylene polyamines products.

Certain phosphoric acid compounds have been disclosed as effective as catalysts in promoting condensation reactions between some amines and tertiary aminoalkanols. However, the reaction conditions are relatively mild. For example, U.S. Pat. No. 3,121,115 to Meuly teaches a process for aminoalkylating certain amines having a replaceable amino hydrogen, particularly aromatic primary and secondary amines, which includes heating the amine compound with an N-tertiary aminoalkanol at from 150° C to 250° C in liquid phase with continuous water removal in the presence of a phosphoric acid compound. The disclosed process requires long reaction times, a disadvantage mentioned hereinbefore, and the use of an N-tertiary aminoalkanol. Thus there is a limitation on the products that can be formed.

We have now discovered an improved catalytic process whereby predominantly mono-N-aminoalkylated piperazine compounds can be produced from the selective dehydration of a primary or secondary aminoalkanol compound with a piperazine compound. The dehydration is somewhat selective to a single or higher oligomeric product. Thus, for example, the mono-N-aminoalkylated compound or the di-N,N'-aminoalkylated compound can be formed to the substantial exclusion of, for example, polyalkylene piperazine compounds. It also has been discovered that the condensation reaction can be carried out under rather severe processing conditions, such as temperatures above about 250° C in liquid phase without the expected decomposition of reactants and products with the attendant formation of high molecular weight polymers.

SUMMARY OF THE INVENTION

In accordance with the broad aspects of the instant invention, N-(aminoalkyl)piperazine compounds are selectively produced directly from a piperazine compound and a primary or secondary aminoalkanol compound having a primary or secondary hydroxy group, by a process which includes contacting the piperazine compound with the alkanolamine compound in the presence of a catalytically effective amount of a phosphorus-containing substance at temperatures of from about 250° to about 350° C under a pressure sufficient to maintain the mixture essentially in liquid phase. The N-(aminoalkyl)piperazines thus produced are then recovered from the resultant reaction mixture.

In accordance with a preferred embodiment, piperazine is contacted with monoethanolamine to produce N-(2-aminoethyl)piperazine.

DESCRIPTION OF THE PREFERRED EMBODIMENT

According to the invention, a piperazine compound or a C-(substituted)piperazine compound is predominantly monoaminoalkylated with a primary or secondary aminoalkanol in the presence of a catalytically effective amount of a phosphorus-containing substance. The reactants are contacted at a temperature of from above about 250° to about 350° C under a pressure sufficient to maintain the reaction mixture essentially in liquid phase. The N-(aminoalkyl)piperazines produced are recovered directly, such as by conventional distillation techniques in high quality yields.

The products selectively formed in practicing the instant invention can be depicted by the general formula

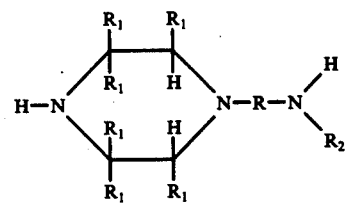

wherein R is a straight chain or branched alkyl radical having from 2 to about 10 carbon atoms, each $R_1$, independently, is hydrogen or an alkyl radical having from 1 to about 5 carbon atoms, and $R_2$ is a hydrogen or an alkyl radical having from 1 to about 18 carbon atoms.

The aminoalkanols which are useful in the practice of this invention can be generally described as primary or secondary aminoalkanols wherein the hydroxy moiety is either primary or secondary. These compounds can be depicted by the formula

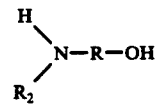

wherein R is a straight chain or branched alkyl radical of from 2 to about 10 carbon atoms, $R_2$ is hydrogen or an alkyl radical of from 1 to about 18 carbon atoms and preferably an alkyl radical of from 1 to about 4 carbon atoms. Illustrative compounds are monoethanolamine, N-ethylpropanolamine, and the like. Preferred aminoalkanols are the primary aminoalkanols, with n-alkyl primary aminoalkanols being most preferred.

Suitable phosphorus-containing substances which can be employed include, for example, acidic metal phosphates, phosphoric acid compounds and their anhydrides, phosphorous acid compounds and anhydrides, alkyl or aryl phosphate esters, alkyl or aryl phosphite esters, alkyl or aryl substituted phosphorous acids and phosphoric acids, alkali metal monosalts of phosphoric acid, the thioanalogs of the foregoing, and mixtures of any of the above.

More particularly, suitable acidic metal phosphates, include boron phosphate, ferric phosphate, aluminum phosphate, etc.

Suitable phosphoric acid compounds include aqueous or anhydrous phosphoric acids such as orthophosphoric acid, pyrophosphoric acid, metaphosphoric acid, and condensed phosphoric acids such as polyphosphoric acids. Accordingly, an example of a suitable phosphorous acid is orthophosphorous acid.

In addition, any commercially available mono-, di-, or tri-alkyl or aryl phosphate or phosphite ester can be employed as the catalyst in the inventive process. Additionally, bis(phosphates) and secondary phosphate esters such as those disclosed in U.S. Pat. Nos. 3,869,526 and 3,869,527, respectively, can be used. Preferably, the lower alkyl esters are employed such as those having from 1 to about 8 carbon atoms per alkyl group. Preferred aryl esters contain from about 6 to about 20 carbon atoms and may include a phenyl group or alkyl-substituted phenyl group.

Further, suitable alkyl or aryl substituted phosphoric acids or phosphorous acids which may be employed as a catalyst include alkyl phosphonic acids, aryl phosphonic acids, alkyl phosphonic acids and aryl phosphinic acids. Preferably, such acids include alkyl or aryl groups and have from 1 to about 8 carbon atoms in each alkyl group and about 6 to about 20 carbon atoms in each aryl group.

Specific examples of alkyl and aryl substituted phosphorous and phorphoric acids that may be used in accordance with the invention are phenylphosphinic, ethylphosphonic, phenylphosphonic, naphthaphosphonic, and methylphosphinic acids. Examples of the alkyl and aryl substituted phosphorous and phosphoric acid esters are methylphenyl phosphonate, dimethylphenyl phosphonate, methylphenyl phosphinate, ethyl naphthaphosphinate, and propylmethyl phosphonate.

The above-mentioned phosphorus compounds are not intended to be exhaustive of those which may be employed as a catalyst material in the process of the present invention.

Those materials are set forth to specify types of phosphorus compounds that we have found to be particularly effective as catalysts. yet, of the compounds and types of compounds mentioned, we especially prefer to employ those that have been found to be most reactive under the processing conditions of the invention. These especially preferred compounds include boron phosphate, aqueous and anhydrous orthophosphoric acid, polyphosphoric acid, aluminum phosphate, ferric phosphate, aqueous and anhydrous orthophosphorous acid, triethylphosphite, triethylphosphate, and diethylphosphite, to name a few. Only a catalytically effective amount of the phosphorus substance is required to effect the condensation reaction between the reactants. The quantity of phosphorus compound employed as the catalyst in the inventive process may vary widely, depending upon its reactivity, the reactants present and particular processing conditions employed. Usually this catalytic amount is within the range of from about 0.01 to about 10.0 wt. %, based upon the amount of aminoalkanol compound material present; and preferably the catalyst is employed in an amount of from about 0.5 to about 5.0 wt. % based upon the amount of alkanolamine compound.

Any of the above-mentioned phosphorus compounds may be employed as the catalyst of the process either alone, in combination with one of the other mentioned phosphorus compounds, or in combination with acidic compounds such as boric acid and the like. These latter acid compounds are generally ineffective as catalysts by themselves in the inventive process.

According to a greatly preferred embodiment, monoethanolamine and piperazine are intimately contacted by admixing. The admixture is heated in the presence of the phosphorus-containing substance at a temperature of from about 250° to about 350° C and preferably at a temperature of about 275° to about 325° C, under a pressure sufficient to maintain the reaction mass in liquid phase which normally ranges from about 200 to about 500 psig. The reaction is allowed to proceed at the temperature employed until the desired amount of conversion is obtained.

The monoethanolamine and the piperazine are contacted for reaction at molar ratios of from about 1:1 to about 1:5. Preferably, the piperazine compound is employed in excess.

Generally the process of the invention can be carried out batchwise or continuously employing well-known batch and continuous processing techniques and conventional processing apparatus. Where the process is carried out continuously, we prefer to employ space velocities of reactants of from about 0.1 to about 4, and preferably from about 0.5 to 1.5, grams total reactants per milliliter of total reactor volume per hour.

In such continuous reaction processes the above described phosphorus-containing catalyst materials may be employed as a feed stream alone or admixed with a reactant feed stream, or they may be employed as a fixed bed catalyst in the continuous reactor system. Generally speaking, these fixed bed catalysts comprise the phosphorus-containing catalyst material supported on a material such as silica, silica-alumina, alumina, diatomaceous earth, etc., conventionally employed as inert reactor packing materials. Such fixed bed supported catalysts and procedures for their preparation are well-known in the art and many are readily available commercially.

It is not critical to control the amount of water of reaction present during the heating of reactants and catalyst, such as by removal thereof as it is formed. Usually, we prefer to retain the water in the reaction zone and remove it from the reaction mass during recovery of the product.

The desired N-(aminoalkyl)piperazines can be readily recovered from the reaction product mass by conventional procedures, such as distillation, without difficulty. For example, the reaction product mass may be directly distilled, or initially filtered to remove a small amount of formed solids which usualy are amine salt complexes of the phosphorus compound catalyst, and then distilled.

The invention will be further illustrated by the following specific example, which is given by way of illustration and not as a limitation the scope of this invention.

EXAMPLE I

Into a 1-liter, cleaned, stainless steel, stirred autoclave was charged 202 g (2.35 moles) piperazine and 102 g (1.67 mole) monoethanolamine and 4.0 g (0.0347 moles)

of 85% aqueous orthophosphoric acid. The autoclave was purged with nitrogen, sealed and the reaction mixture heated with stirring at a temperature of about 280° C for 2.0 hours under a pressure of 250-360 psig. The crude reaction product mixture was recovered and water of reaction and lights were removed by distillation and the remaining residue cooled. The cooled residue was dissolved in methanol and analyzed by gas liquid chromatography (Area %, lights, water free). Analysis showed the following: 52.7 A% piperazine, 11.0 A% monoethanolamine, and 28.7 A% N-(2-aminoethyl)piperazine. Based upon the conversion of reactants, the theoretical conversion to N-(2-aminoethyl)-piperazine was calculated as 36.3 wt.%.

EXAMPLE II

In a stirred, one liter autoclave, 252 g (2.93 moles) of piperazine, 126 g (2.06 moles) of monoethanolamine and 6 g of 30% phosphorous acid were stirred under a nitrogen atmosphere for 2 hours. The reaction temperature was held at 300° C while the reaction pressure increased from 375 to 525 psig during the run. The high colored product was analyzed by gas chromatography on a water free basis and found to contain, by area percent, 8.4% monoethanolaine, 48.8% piperazine and 32.3% 1-(2-aminoethyl)piperazine.

While the invention has been explained in relation to its preferred embodiment, it is to be understood that various modifications thereof will become apparent to those skilled in the art upon reading the specification and is intended to cover such modifications as fall within the scope of the appended claims.

What is claimed is:

1. A process for producing an N-(aminoalkyl)piperazine compound directly from a piperazine compound selected from piperazine and C-(substituted) piperazine wherein the substituents are alkyl radicals having from 1 to 5 carbon atoms and a primary and secondary aminoalkanol compound having a primary hydroxy group of the formula:

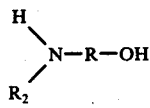

wherein R is a branched or straight chain alkyl radical having from 2 to 10 carbon atoms and $R_2$ is hydrogen or an alkyl radical having from 1 to about 4 carbon atoms, comprising the steps of:
contacting said piperazine compound with said alkanolamine compound in the presence of a catalytically effective amount of a phosphorus-containing substance selected from the group consisting of acidic metal phosphates, phosphoric acids and their anhydrides, or phosphorous acids and their anhydrides, alkyl or aryl phosphate esters, alkyl or aryl phosphite esters, alkyl or aryl substituted phosphorous acids and phosphoric acids, alkali metal monosalts of phosphoric acid, the thioanalogs of the foregoing, and mixtures thereof at temperatures of from about 250° to about 350° C under a pressure sufficient to maintain the mixture essentially in liquid phase; and,
recovering the N-(aminoalkyl)piperazine thus produced from the resultant reaction mixture.

2. The process in accordance with claim 1 wherein said contacting is accomplished at a temperature of from about 275° to about 325° C.

3. The process in accordance with claim 1 wherein said contacting is accomplished at a pressure ranging from about 200 psig to about 500 psig.

4. The process in accordance with claim 1 wherein said phosphorus-containing substance is phosphorous acid.

5. The process in accordance with claim 1 wherein said phosphorus-containing substance is present in an amount of from about 0.1 to about 10.0 wt. % based upon the amount of said aminoalkanolamine present.

6. The process in accordance with claim 1 wherein said piperazine compound is piperazine, said aminoalkanol is monoethanolamine and said phosphorus containing compound is ortho phosphoric acid.

7. The process in accordance with claim 1 wherein said aminoalkanol is a n-alkyl primary aminoalkanol; and wherein said piperazine compound is piperazine.

8. The process of claim 7 wherein said phosphorus containing substance is selected from boron phosphate, aqueous and anhydrous orthophosphoric acid, polyphosphoric acid, aluminum phosphate, ferric phosphate, aqueous and anhydrous orthophosphorous acid, triethylphosphite, triethylphosphate, and diethylphosphite.

* * * * *